United States Patent
Kibalo

(10) Patent No.: US 9,023,273 B2
(45) Date of Patent: May 5, 2015

(54) METHOD FOR PROCESSING TISSUES

(75) Inventor: Benjamin Kibalo, Bridgewater Township, NJ (US)

(73) Assignee: LifeCell Corporation, Branchburg, NJ (US)

( * ) Notice: Subject to any disclaimer, the term of this patent is extended or adjusted under 35 U.S.C. 154(b) by 451 days.

(21) Appl. No.: 12/858,065

(22) Filed: Aug. 17, 2010

(65) Prior Publication Data
US 2011/0044847 A1 Feb. 24, 2011

Related U.S. Application Data

(60) Provisional application No. 61/234,681, filed on Aug. 18, 2009.

(51) Int. Cl.
*A61L 2/00* (2006.01)
*C12N 5/00* (2006.01)
*A61K 35/36* (2006.01)

(52) U.S. Cl.
CPC ..................................... *A61K 35/36* (2013.01)

(58) Field of Classification Search
CPC ............. A61L 2/08; A61L 2/02; A61K 35/36
USPC ........................................ 422/22, 1; 435/378
See application file for complete search history.

(56) References Cited

U.S. PATENT DOCUMENTS

| 5,336,616 | A | 8/1994 | Livesey et al. | |
|---|---|---|---|---|
| 7,108,832 | B2 * | 9/2006 | Christensen et al. | 422/28 |
| 2005/0186286 | A1 * | 8/2005 | Takami | 424/572 |
| 2006/0110720 | A1 * | 5/2006 | Fujisato et al. | 435/1.1 |
| 2008/0027562 | A1 | 1/2008 | Fujisato et al. | |
| 2008/0166266 | A1 * | 7/2008 | Burns et al. | 422/33 |

FOREIGN PATENT DOCUMENTS

| EP | 1541157 | 6/2005 |
|---|---|---|
| EP | 2138181 | 12/2009 |
| JP | 2004-097552 A | 4/2004 |
| JP | 2006-261933 A | 9/2006 |
| WO | WO 2007/123684 | 11/2007 |
| WO | WO 2008/111530 | 9/2008 |
| WO | WO 2008/154621 | 12/2008 |

OTHER PUBLICATIONS

English Translation of International Publication No. WO 2008/111530 A1 provided by the World Intellectual Property Organization Website: Kishida, Akio; Method of Preparing Decellularized Soft Tissue, Graft and Culture Material; Aug. 9, 2008 http://www.wipo.int/wipogold/en/.*

(Continued)

*Primary Examiner* — Kevin Joyner

(74) *Attorney, Agent, or Firm* — McCarter & English, LLP; Jonathan M. Sparks; Matthew R. Van Eman

(57) ABSTRACT

Methods for processing tissue are provided. In some embodiments, the methods comprise methods for decellularizing tissue samples by applying high hydrostatic pressure to the tissues samples. In some embodiments, the methods comprise methods for thawing tissue samples and/or reducing the bioburden in a sample by applying high hydrostatic pressure to the tissue samples.

14 Claims, 4 Drawing Sheets

(56) References Cited

OTHER PUBLICATIONS

Alpas et al., "Inactivation of *Alicyclobacillus acidoterrestris* vegetative cells in model system, apple, orange and tomato juices by high hydrostatic pressure," World J. Microbiol. Biotechnol. 19:619-623 (2003).

Alpas et al., "Variation in Resistance to Hydrostatic Pressure among Strains of Food-Borne Pathogens," Appl. Environ. Microbiol. 65(9):4248-4251 (1999).

Aoyama et al., "Non-thermal Inactivation of *Bacillus* Spores by Pressure-holding," Food Sci. Technol. Res. 11(3):324-327 (2005).

Considine et al., "High-pressure processing—effects on microbial food safety and food quality," FEMS Microbiol. Lett. 281:1-9 (2008).

Delacour et al., "Inactivation des spores bactériennes par les hautes pressions hydrostatiques," Ann. Pharm. Fr. 60:38-43 (2002). French.

Diehl et al., "Biomechanical and immunohistochemical analysis of high hydrostatic pressure-treated Achilles tendons," J. Orthop. Sci. 11:380-385 (2006).

Diehl et al., "Effect of high hydrostatic pressure on biological properties of extracellular bone matrix proteins," Int. J. Mol. Med. 16:285-289 (2005).

Diehl et al., "High Hydrostatic Pressure, a Novel Approach in Orthopedic Surgical Oncology to Disinfect Bone, Tendons and Cartilage," Anticancer Res. 28:3877-3883 (2008).

Dogan et al., "High pressure inactivation kinetics of *Listeria monocytogenes* inactivation in broth, milk, and peach and orange juices," J. Food Eng. 62:47-52 (2004).

Fonberg-Broczek et al., "High pressure processing for food safety," Acta Biochim. Pol. 52(3):721-724 (2005).

Furukawa et al., "Mechanical Analysis of the Injury of Spores by Reciprocal Pressurization," Food Sci. Technol. Res. 10(1):13-16 (2004).

Kleber et al., "Antigenic response of bovine β-lactoglobulin influenced by ultra-high pressure treatment and temperature," Innovative Food Science & Emerging Technologies, 8:39-45 (2007).

Luscher et al., "Effect of High-Pressure-Induced Ice I-to-Ice III Phase Transitions on Inactivation of *Listeria innocua* in Frozen Suspension," Appl. Environ. Microbiol. 70(7):4021-4029 (2004).

Masson, "Action de la pression hydrostatique sur les protéines: émergence de la biotechnologie des hautes pressions, applications pharmaceutiques et médicales potentielles," Ann. Pharm. Fr. 57:49-55 (1999). French.

Torres et al., "Commercial opportunities and research challenges in the high pressure processing of foods," J. Food Eng. 67:95-112 (2005).

van Doorne, "High-Pressure Treatment, a Potential Antimicrobial Treatment for Pharmaceutical Preparations? A Survey," J. Pharm. Sci. Technol. 62(4):273-291 (2008).

Zhao et al., "High Hydrostatic Pressure Effects on Rapid Thawing of Frozen Beef," J. Food Sci. 63(2):272-275 (1998).

Funamoto et al., "The use of high-hydrostatic pressure treatment to decellularize blood vessels," Biomaterials 31:3590-3595 (2010).

Gilbert et al., "Decellularization of tissues and organs," Biomaterials 27:3675-3683 (2006).

Hashimoto et al., "Preparation and characterization of decellularized cornea using high-hydrostatic pressurization for corneal tissue engineering," Biomaterials 31:3941-3948 (2010).

Hashimoto et al., "Preparation of Acellularized Bone Using High Pressure Technology for Tissue Engineering," 2006, retrieved from the internet: URL:http://aiche.confex.com/aiche/2006/techprogram/P64482.htm [retrieved on Nov. 11, 2010].

Kimura et al. "Preparation and Characterization of Cornea Decellularized by Ultra High Pressurization," Tissue Engineering 13(7):1746-1747 (2007), Abstract.

Murakoshi et al., "Effect of the Pressurizing Process on the Decellularized Aortic Tissue Using Ultra High Hydrostatic Pressurization," Tissue Engineering 13(7):1680 (2007), Abstract.

Partial International Search for PCT/US2010/045723 mailed Dec. 2, 2010, from the European Patent Office.

Sasaki et al., "In vivo evaluation of a novel scaffold for artificial corneas prepared by using ultrahigh hydrostatic pressure to decellularize porcine corneas," Molecular Vision 15:2022-2028 (2009).

Toldrà et al., "Functional and quality characteristics of the red blood cell fraction from biopreserved porcine blood as influenced by high pressure processing," Meat Science 80:380-388 (2008).

Yin Meng et al., "Tissue-engineered vascular scaffolds prepared by ultrahigh pressure decellularization treatment," Journal of Clinical Rehabilitative Tissue Engineering Research 12(10):1969-1973 (2008).

Cheftel et al., "Pressure-assisted freezing and thawing: Principles and potential applications," *Food Rev. Int.* 16(4):453-483 (2000).

International Search Report and Written Opinion for PCT/US2010/045723 mailed Mar. 22, 2011, from the International Searching Authority of the European Patent Office.

Karow, Jr. et al., "Survival of dog kidneys subjected to high pressures: Necrosis of kidneys after freezing," *Cryobiology* 7(2-3):122-128 (1973).

LeBail et al., "High pressure freezing and thawing of foods: a review," *Int. J. Refrigeration* 25:504-513 (2002).

Otero et al., "High pressure-assisted and high pressure-induced thawing: Two different processes," *J. Food Science* 68(8): 2523-2528 (2003).

Picart et al., "Combined high pressure—sub-zero temperature processing of smoked salmon mince: phase transition phenomena and inactivation of *Listeria innocua*," *J. Food Eng.* 68:43-56 (2005).

Smelt, "Recent advances in the microbiology of high pressure processing," *Trends in Food Science & Technology* 9:152-158 (1998).

Eckert, Charles A. et al., "Supercritical fluids as solvents for chemical and materials processing", *Nature*, vol. 383, Sep. 26, 1996, pp. 313-318.

Jessop, Phillip G., et al., "Homogeneous catalytic hydrogenation of supercritical carbon dioxide", *Nature*, vol. 368, Mar. 17, 1994, pp. 231-233.

Poliakoff, Martyn et al., "A supercritical success story", *Chemistry & Industry*, Oct. 4, 1999, pp. 750-752.

Poliakoff, Martyn, et al., "Intermediates in organometallic and organic chemistry: spectroscopy, polymers, hydrogenation and supercritical fluids", Journal of Physical Organic Chemistry, vol. 11, (1998), pp. 589-596.

Spilimbergo, S. et al., "Non-Thermal Bacteria Inactivation With Dense $CO_2$", *Biotechnology and Bioengineering*, vol. 84, No. 6, Dec. 20, 2003, pp. 627-638.

White, Angela, "Effective terminal sterilization using supercritical carbon dioxide", *Journal of Biotechnology*, 123 (2006), pp. 504-515.

\* cited by examiner

METHOD FOR PROCESSING TISSUES

This application claims priority under 35 U.S.C. §119 to U.S. Provisional Patent Application No. 61/234,681, which was filed on Aug. 18, 2009.

Human and animal tissues can be used to produce a variety of tissue products for patient use. The tissues are often processed to remove certain cellular and/or non-cellular components and/or to destroy pathogens present in the tissues. In addition, during processing or storage, tissues may be frozen and thawed.

SUMMARY

According to certain embodiments, a method for decellularizing a tissue sample is provided, which comprises providing a tissue sample comprising a mammalian soft tissue in a liquid; and applying a pressure to the liquid of at least 200 MPa for a time sufficient to destroy substantially all of the native tissue cells within the soft tissue, wherein destroying substantially all of the cells includes disrupting the cell membrane of the cells such that washing the tissue sample in a saline solution allows removal of at least 95% of the native tissue cells.

According to certain embodiments, a method for thawing a tissue sample is provided, which comprises providing a tissue sample comprising a mammalian tissue that is at least partially frozen in a liquid; and applying a pressure to the liquid sufficient to thaw the frozen tissue sample.

According to certain embodiments, a method for decellularizing a tissue sample is provided, which comprises providing a tissue sample comprising a mammalian tissue in a container containing liquid; and applying a pressure to the liquid for a time sufficient to destroy substantially all of the cells within the soft tissue, wherein destroying substantially all of the cells includes disrupting the cell membrane of the cells such that washing the tissue sample in a saline solution allows removal of at least 95% of the native tissue cells. and wherein the pressure is applied at a rate such that the temperature of the tissue sample does not exceed 30° C.

According to certain embodiments, a method for reducing the bioburden in a tissue sample is provided, which comprises providing a tissue sample comprising a mammalian soft tissue in a container containing liquid; and applying a pressure to the liquid for a time sufficient to cause at least a 5 log reduction in the bacterial concentration within the soft tissue, wherein during application of the pressure, the temperature of the tissue sample does not exceed 30° C.

DESCRIPTION OF CERTAIN EXEMPLARY EMBODIMENTS

Figure 1:
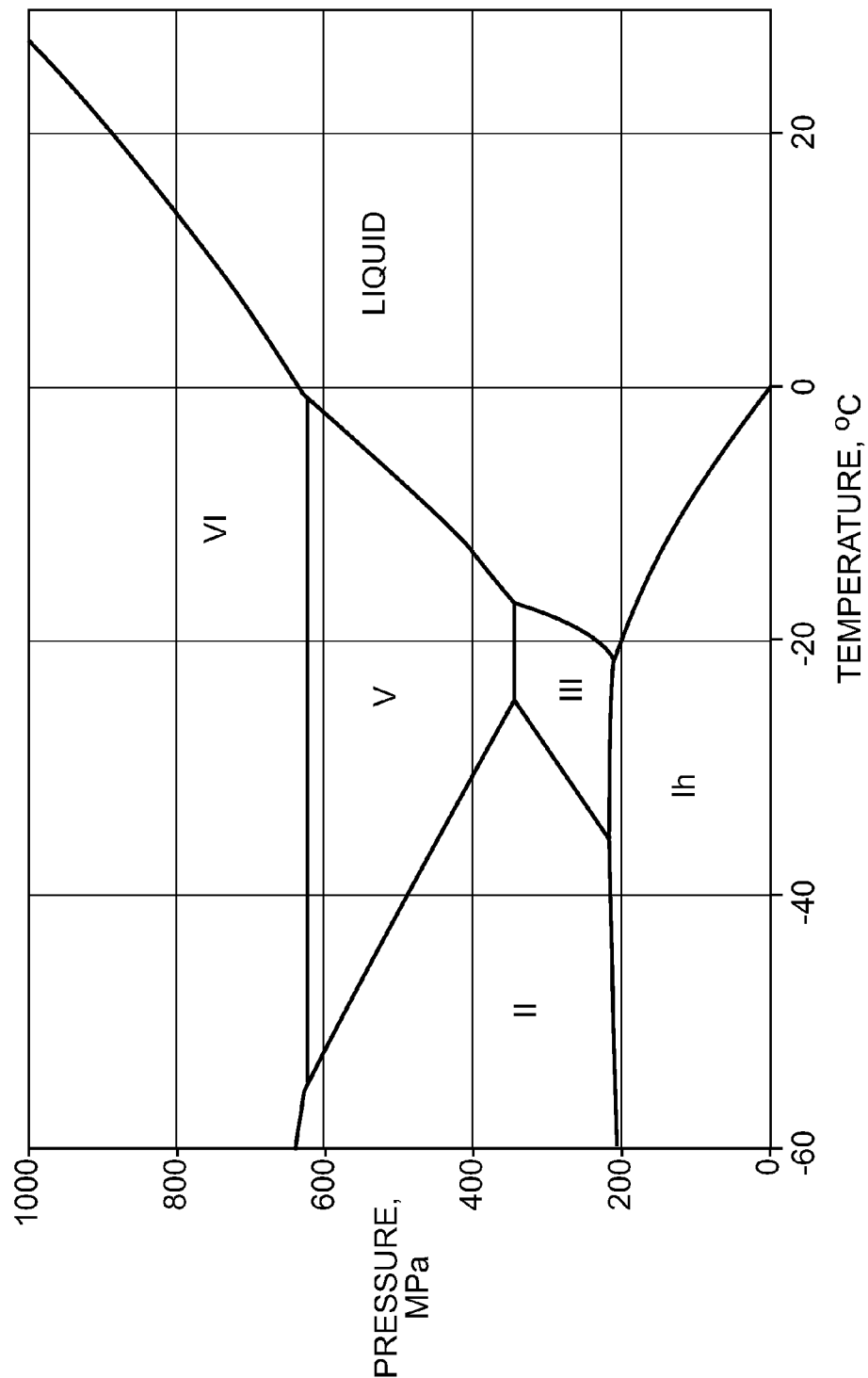
FIG. 1 is a phase diagram for water.

Reference will now be made in detail to the certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

As used herein, "high hydrostatic pressure" is understood to refer to pressure applied to an object contained in a liquid, the liquid being pressurized to exert force on the object. In certain embodiments, high hydrostatic pressure can include pressures applied to the liquid that are greater than 200 MPa.

As used herein, "bioburden" means the quantity of microorganisms in a tissue sample, including, but not limited to, bacteria, viruses, fungi, parasites, chlamydiae, rickettsiae, mycoplasma, and protozoa.

As used herein, "tissue products" or "tissue-derived products" means any product produced from a tissue that has been altered in any way (e.g., but not limited to, by removing cells from the tissue, removing certain chemicals from the tissue, or sterilizing the tissue). As used herein, "tissue samples" include both intact, unprocessed tissues and tissues that have been processed to produce "tissue products" or "tissue-derived products."

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, tissue matrices and/or tissue-derived proteins or protein-containing materials (e.g., glycosaminoglycans) that can be used alone or in combination with other materials and/or chemicals.

In certain embodiments, these products can be completely or partially decellularized to yield tissue matrices or extracellular tissue materials to be used for patients. For example, various tissues, such as skin, intestine, bone, cartilage, nerve tissue (e.g., nerve fibers or dura), tendons, ligaments, or other tissues can be completely or partially decellularized to produce tissue products useful for patients. In some cases, these decellularized products can be used without addition of exogenous cellular materials (e.g., stem cells). In certain cases, these decellularized products can be seeded with cells from autologous or other sources to facilitate treatment.

Since tissue products are often implanted on or within a patient's body, in certain embodiments, it is desirable to sterilize such materials, or at least reduce the amount of bacteria or other pathogens that might be in the products, to a level acceptable for the selected use. In certain embodiments, various tissues, tissue-derived products, and other implantable medical devices are typically sterilized using processes such as irradiation (e.g., gamma, E-beam or X-ray), treatment with chemicals, or heat.

For use in various medical or surgical applications, tissues or tissue products should possess desired biologic properties, depending on the intended use. For example, tissue products used for tissue regeneration should generally be capable of supporting or inducing cellular ingrowth and/or regeneration. However, certain tissue processing techniques can damage some tissues and/or remove portions of the tissue that may be desirable for certain biologic functions. For example, in certain embodiments, tissue decellularization processes can include the use of various enzymes, detergents, and/or chemicals that may damage or remove various cell signal molecules or extracellular matrix proteins desired for regeneration or growth of certain tissues. In addition, in certain embodiments, sterilization techniques, such as gamma irradiation, can alter tissue products by causing breakdown and/or chemical alteration of such products.

The present disclosure provides methods of processing tissue samples that maintain certain desired biologic properties of tissue products produced using such methods. In some embodiments, the methods comprise a method for decellularizing a tissue sample. In certain embodiments, the methods comprise a method for thawing a tissue sample. In some embodiments, the methods comprise a method for reducing the bioburden of a tissue sample.

In some embodiments, the methods for processing tissue samples can include application of a high hydrostatic pressure to a tissue. In certain embodiments, high hydrostatic pressure can be applied to a tissue sample by placing a tissue sample in a liquid or providing a tissue in a liquid. In certain embodiments, pressure can be applied to the liquid, thereby controlling the pressure applied to the tissue sample. In various embodiments, the pressure applied to the tissue sample, the time that the pressure is applied, and/or the rate of pressure increase and/or decrease can be controlled to decellularize the tissue sample, reduce the bioburden in the tissue sample, and/or thaw the tissue sample.

In various embodiments, the pressure applied to the tissue sample can be selected based on a variety of factors. In some embodiments, the pressure is selected based on the type of tissue sample to be processed. In some embodiments, the pressure is selected to allow decellularization of the tissue sample while maintaining certain desired biologic properties of the tissue sample. In some embodiments, the pressure is selected to allow the tissue to be thawed without raising the tissue sample above a selected temperature and/or to allow thawing within a selected time.

In various embodiments, the methods of the present disclosure can be used to process a variety of different tissue sample types. Exemplary mammalian tissues samples include, but are not limited to, bone, skin, intestine, urinary bladder, tendon, ligament, muscle, fascia, neurologic tissue, liver, heart, lung, kidney, cartilage, and/or other mammalian tissue. In certain embodiments, the tissue sample can include a mammalian soft tissue sample. For example, in certain embodiments, the tissue sample can include mammalian dermis. In certain embodiments, the dermis can be separated from surrounding epidermis and/or other tissues, such as subcutaneous fat. In certain embodiments, the tissue sample can include small intestine submucosa. In certain embodiments, the tissue samples can include human or non-human sources. Exemplary, suitable non-human tissue sources include, but are not limited to, pigs, sheep, goats, rabbits, monkeys, and/or other non-human mammals.

Various types of high hydrostatic pressure application systems can be used to process tissue samples according to certain embodiments. In certain embodiments, a high hydrostatic pressure application system will include a rigid vessel or container formed of steel or other hard material. In certain embodiments, a tissue sample to be treated is placed in the vessel along with a fluid (e.g., water). In certain embodiments, the tissue sample may be packaged in a flexible container that also contains fluid, and the flexible package may be placed in a vessel containing fluid. In certain embodiments, after the vessel is loaded with the tissue sample and fluid, pressure is applied to the fluid in the vessel. In certain embodiments, the pressure can be applied in a number of ways. For example, in certain embodiments, the pressure can be applied using a pneumatic piston to compress the fluid in the vessel, or a pump can force additional fluid into the vessel until the pressure in the vessel reaches a desired level.

In certain embodiments, a tissue sample is packaged in a flexible container containing a liquid, and pressure is applied to the container. In some embodiments, a tissue sample is placed in a rigid pressurization container containing a liquid and pressure is applied to the liquid in the rigid container. In some embodiments, the tissue sample is packaged in a flexible container containing a liquid, and the flexible container is placed in a rigid pressurization container containing a liquid, and pressure is applied to the liquid in the rigid container. In various embodiments, the pressure can be applied to the fluid by compressing the fluid using, for example, a piston, or by pumping addition fluid into a container with a fixed volume. In certain embodiments, when the tissue sample is packaged in a flexible container, generally, the flexible container is sealed so that only the fluid inside the flexible container contacts the tissue sample.

A variety of liquids can be used to contact the liquid during application of high hydrostatic pressure. For example, various aqueous solutions can be used. In certain embodiments, the liquid can include an aqueous salt. In certain embodiments, the liquid can include a saline solution, such as a phosphate buffered saline.

In some embodiments, the tissue sample can be processed to destroy some or substantially all of the native tissue cells of the tissue sample. In certain embodiments, determination that destruction of the native tissue cells has been accomplished can be performed by washing a tissue sample that has been treated with high hydrostatic pressure with a liquid that does not damage the cells significantly (e.g., PBS) and analyzing the samples to determine how much, if any, of the native tissue cells remain. For example, in some embodiments, after high hydrostatic pressure treatment to destroy cells, simple washing with a saline solution can remove cell remnants, and the washed sample can be evaluated to determine if the cells have been removed, thereby indicating destruction of the cells. Certain suitable methods for evaluating the samples to determine if cells have been destroyed and removed are well known, and include for example, but are not limited to, light microscopy of frozen or fixed tissue cells. In certain embodiments, the presence of cells or cell remnants can be evaluated using reagents that indicate that DNA is present, for example, PICOGREEN® DNA quantification kits can be used.

As used herein, destruction of substantially all of the cells will be understood to mean that at least 95% to 100%, including the endpoints and all percentages between those end points, of the native tissue cells of a tissue sample that has been treated with high hydrostatic pressure and washed in a saline solution are not present when evaluated using conventional histology (e.g., light microscopy).

In some embodiments, tissue samples may be treated with high hydrostatic pressure to remove some or substantially all of the cells in the tissue sample, and the tissue sample may be treated further with other processes to remove remaining cells. For example, as noted above, in various embodiments, various enzymes, detergents, and/or other chemicals are used to remove cells from tissues, but such treatments may alter tissue extracellular matrices. Therefore, to reduce the amount of treatment with enzymes, detergents, and/or other chemicals, tissue samples may first be treated with a high hydrostatic pressure treatment, thereby removing some or substantially all of the cells, and the tissue sample may be treated further with at least one additional decellularization process to remove additional cells, if any are present in the tissue sample. Suitable reagents and methods for performing decellularization include, but are not limited to, those described in, for example, U.S. Pat. No. 5,336,616, to Livesey et al.

In some embodiments, the tissue sample may be processed to produce an acellular tissue matrix. In some embodiments, the acellular tissue matrix can include an extracellular matrix. For example, in various embodiments, the tissue matrix can include a collagen matrix derived from a variety of different mammalian soft tissues. In certain embodiments, the tissue matrix can include one or more additional extracellular matrix proteins and/or molecules, including, but not limited to, various GAGs, cell-signaling molecules, or other chemicals desired for effecting various biologic functions, such as cell binding, adhesion, growth, differentiation, and/or remodelling.

In some embodiments, a method for decellularizing a tissue sample comprises providing a tissue sample comprising a mammalian soft tissue in a liquid and applying a pressure to the liquid for a time sufficient to destroy substantially all of the native tissue cells within the soft tissue. In some embodiments, the pressure is applied at a minimum pressure to destroy substantially all of the native tissue cells within the soft tissue. In various embodiments, the pressure is at least 200 MPa, at least 300 MPa, at least 400 MPa, or at least 500 MPa. In various embodiments the pressure is between 300 MPa and 500 MPa. In various embodiments, the pressure is applied for a time sufficient to destroy substantially all of the native tissue cells within the soft tissue. In various embodiments, the pressure is applied for at least 30 minutes to at least 60 minutes. In certain embodiments, the pressure applied to the liquid is at least 400 MPa for at least 10 minutes. In certain embodiments, the pressure applied to the liquid is at least 400 MPa for at least 30 minutes. In certain embodiments, the pressure applied to the liquid is at least 500 MPa for at least 30 minutes. In various embodiments, the methods of decellularization are performed without causing excessive heating of the tissue sample, as described below.

In various embodiments, the methods of the present disclosure allow application of high hydrostatic pressure to a tissue sample without causing significant heating of the tissue sample. In various embodiments, heating of certain tissue samples may damage various tissue extracellular matrix proteins, thereby diminishing desired biologic functions of the tissue samples when used for tissue repair, replacement, or regeneration. Therefore, certain embodiments herein can allow tissue decellularization, tissue thawing, and/or reduction in tissue bioburden without heating the tissue samples to a temperature or for a time that may damage tissue extracellular matrix proteins. In certain embodiments, high hydrostactic pressure is applied at a rate and to a maximum pressure such that the tissue sample does not reach a temperature greater than 30° C. In certain embodiments, the temperature does not exceed 25° C.

In certain embodiments, application of pressure in a hydrostatic pressure vessel causes adiabatic compression of the materials within the vessel (i.e., the liquid), which causes the temperature of the compressed materials to increase. However, certain pressurization vessels allow some heat transfer through the walls of the vessel, and therefore, such systems are not truly adiabatic. Therefore, in various embodiments, the amount of pressure increase is related to the rate of compression (i.e., pressure increase) and heat transfer to or from the vessel walls. In addition, in various embodiments, phase changes of the water within the vessel can also affect temperature within the vessel. Therefore, in some embodiments, the temperature of the sample being treated with high hydrostatic pressure can be controlled by controlling the rate of pressure increase in the treatment vessel.

In certain embodiments, the tissue sample, liquid contained in a pressurization vessel, and/or pressurization equipment can be cooled before and/or during application of high hydrostatic pressure. In some embodiments, ice may be placed in the liquid contained in the pressurization vessel, and/or the walls of the pressurization vessel can be cooled.

In various embodiments, to prevent tissue damage, breakdown, and/or microbial growth, it is often desirable to freeze tissue samples during processing, transport, and/or storage. In various embodiments, during subsequent processing or use, the tissue sample is thawed. But, in certain instances, thawing by heating the tissue sample can damage tissue extracellular matrix components and/or promote microbial growth. Further, in certain embodiments, thawing tissue samples under relatively cool conditions (e.g. under refrigeration or just above the freezing point of water in the sample) can be time consuming, especially for larger tissue samples.

In certain embodiments, a method for thawing a tissue sample comprises providing a tissue sample comprising a mammalian tissue that is at least partially frozen in a liquid and applying a pressure to the liquid sufficient to thaw the frozen tissue sample. In some embodiments, thawing occurs within a limited time and/or with only limited elevation of the tissue sample temperature.

FIG. 1 provides a phase diagram for solid and liquid phases of water. As shown, the melting point of various ice phases decreases at higher pressures. Therefore, in certain embodiments, application of elevated hydrostatic pressures to samples containing ice can cause conversion of the solid state water to liquid without significant heating of the tissue sample.

In various embodiments, a tissue sample can contain water that is partially or entirely solid state (i.e., ice). In various embodiments, thawing the tissue sample comprises causing a portion or substantially all of the solid-state water in the sample to be converted to liquid. In some embodiments, thawing the frozen tissue sample comprises causing greater than 50% of the solid state water in the tissue sample to undergo a phase transformation to a liquid state. In some embodiments, thawing the frozen tissue comprises causing substantially all of the solid state water in the tissue sample to undergo a phase transformation to a liquid state. In various embodiments, between 50% to 100% of the ice in the sample undergoes a phase transformation to a liquid state.

In various embodiments, the amount of solid state ice in the sample before and after application of a high hydrostatic pressure treatment can be determined in several ways. For example, in various embodiments, the presence of ice in a sample can be determined using small samples for differential scanning calorimetry (DSC). For larger samples, in various embodiments, ice can be identified by placing a sample in a thermally insulated liquid at a known temperature and supplying heat to the system. In certain embodiments, samples can be compressed (pressurized) in an adiabatic system, and the sample temperature or the temperature of a fluid media surrounding the sample can be measured during compression. Samples that have no ice will be expected to increase their temperature in an adiabatic system at a constant rate related to the pressurization rate. In certain embodiments, for samples containing ice, the temperature of the samples will plateau at a temperature near the melting point of ice. In some embodiments, if the temperature of the fluid surrounding the sample is measured, the fluid temperature will increase more slowly for samples containing ice than for samples that do not contain ice. The plateau in sample temperature and/or decrease in the rate of temperature rise will be dependent on the amount of ice present.

In some embodiments, the temperature of a tissue sample undergoing high hydrostatic pressure treatment is maintained below an upper limit. In some embodiments, the upper limit is based on the initial temperature of the sample. For example, in some embodiments, the thawing of the tissue is performed without increasing the temperature of the tissue sample more than 10° C. In some embodiments, the thawing is performed without increasing the temperature above 30° C. In some embodiments, the thawing is performed without increasing the temperature above 25° C. In certain embodiments, the thawing is performed without increasing the temperature of the tissue sample above between about 25° C. and 30° C.

In some embodiments, the thawing is performed without increasing the temperature above an upper limit, and within a certain time. For example, in some embodiments, thawing occurs within 30 minutes. In certain embodiments, thawing occurs within 60 minutes. In various embodiments, thawing occurs in between about 30 minutes and about 60 minutes.

In various embodiments, the high-hydrostatic pressure treatment is performed to obtain a certain level of reduction in sample bioburden. For example, in various embodiments, high hydrostatic pressure may be applied at a pressure and time sufficient to cause a pressure and time sufficient to cause at least a 5 log reduction, a 6 log reduction, a 7 log reduction, or an 8 log reduction in the bacterial load of a sample. In some embodiments, high hydrostatic pressure may be applied at a pressure and time sufficient to reduce the bioburden to a particular level.

In various embodiments, the bioburden of a tissue sample can be measured by extracting microbes from a tissue sample and culturing or quantifying a particular type of organism. A suitable method for extracting microbes from a sample includes washing a sample with a sterile liquid and culturing a portion or all of the liquid used to wash the sample in order to quantify the amount of any particular microbe or microbes in a sample. In various embodiment, the washing fluid can be selected based on the type of microbe to be quantified and/or to prevent damage to the tissue. In some embodiments, the bioburden reduction is performed without increasing the temperature above 30° C. In some embodiments, the bioburden reduction is performed without increasing the temperature above 25° C. In certain embodiments, the bioburden reduction is performed without increasing the temperature of the tissue sample above between about 25° C. and 30° C.

In some embodiments, a sterilization process can be performed before or after applying high hydrostatic pressure to a tissue sample. For example, in some embodiments, application of high hydrostatic pressure will at least partially reduce the bioburden of a tissue sample, and a tissue sterilization process can be performed to further reduce the bioburden in the sample. In some embodiments, the sterilization process can be a terminal sterilization process that is performed just before or after packaging a tissue sample. As used herein, a "sterilization process" can include any process that reduces the bioburden in a sample, but need not render the sample absolutely sterile.

Certain exemplary processes include, but are not limited to, a gamma irradiation process, an e-beam irradiation process, a supercritical carbon dioxide sterilization process, and a per-acetic acid treatment process. In various embodiments, such processes may damage some tissue components, and, therefore, to produce tissues having desired biologic properties, it may be desirable to limit the time or intensity (e.g., radiation dose or pH) of the sterilization process. In certain embodiments, application of high hydrostatic pressure to a sample to partially reduce the bioburden can therefore reduce the dose of subsequent sterilization processes used to achieve a desired level of sterility. Suitable sterilization processes include, but are not limited to, those described in, for example, U.S. Patent Publication No. 2006/0073592A1, to Sun et al.; U.S. Pat. No. 5,460,962, to Kemp; U.S. Patent Publication No. 2008/0171092A1, to Cook et al.

EXAMPLE 1

Reduction in Tissue Bioburden

Porcine skin was used. The tissue was provided either as whole skin with hair intact or as dermal layers that were isolated from the epidermis and subdermal fat layers. The dermal layer was isolated by cutting the subdermal fat and a thin layer (1-2 mm) of the lower dermis from the dermis, and by cutting a thin layer (0.25-1 mm) of the epidermis and upper dermis from the dermis. Hair was mechanically removed before isolating the dermis. Both sample types were previously frozen, and to increase the bioburden levels in isolated dermis tissue, all of the tissue was stored together (whole skin and isolated dermis) for several days after thawing under refrigerated conditions. Each piece was individually packaged using a DENI™ Magic Vac food saver device. Each piece was sealed within three vacuum sealed pouches to prevent exposure of porcine tissue to the pressurization vessel. The samples were packaged with a minimum amount of fluid in the sealed pouch such that the package closely conformed to the sample.

A 13 liter pressurization system made by ElmHurst Research, Inc (Albany, N.Y.) was used for the experiments. The system had a fixed volume and applied pressure by pumping fluid into the vessel. The temperature was measured using a thermocouple that protruded from the cap of the vessel into the pressurization chamber to measure bulk fluid pressure.

Small pieces of both whole skin and isolated dermis were tested first (runs 1 and 2), and large non-dehaired pieces were exposed to the same conditions (runs 3 and 4). Table 1 summarizes these conditions. The pressure vessel had no temperature control system, so the maximum temperature was dependant mainly on the initial temperature and maximum pressure. The rate of pressure increase was at a single speed of 350 PSI/sec. After runs 1 and 2, the small pieces of tissue that were exposed to high hydrostatic pressure were examined by eye and touch for obvious signs of degradation. No obvious signs of degradation were seen, so the large pieces of tissue were processed in runs 3 and run 4.

TABLE 1

| | Run Conditions | | | |
| --- | --- | --- | --- | --- |
| Run # | Pressure (PSI) | Time (min) | Start Temp (C.) | Max Temp (C.) |
| 1 and 3 | 60,000 | 5 | 27.0 and 25.3 | 38.7 and 38.8 |
| 2 and 4 | 75,000 | 10 | 26.8 and 25.7 | 39.9 and 40.5 |

After exposure, the tissue samples were stored in refrigerated conditions (1-10° C.) for less than 1 week. Samples of the whole skin and isolated dermis and were submitted for bioburden testing. The samples were agitated in a PBS solution to extract the bacteria from the samples, and the PBS solution was plated on an agar plate and incubated. Bacterial colonies were counted. Control samples of untreated tissue (both isolated dermis and whole skin) were also subjected to the same bioburden testing before exposure to high hydrostatic pressure.

After refrigeration, some remaining isolated dermal tissue samples were also subjected to DSC. DSC was performed using 12-23 mg of sample on a TA Differential Scanning calorimeter (TA Instruments, New Castle, Del.).

Figure 2A:
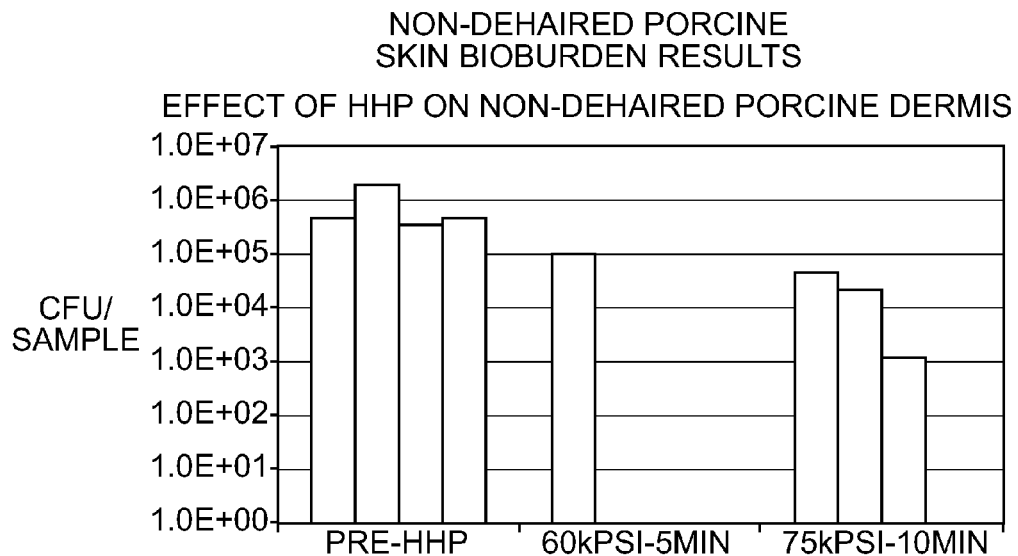
FIG. 2A is bioburden test result data for whole porcine skin samples, as described in Experiment 1.
Figure 2B:
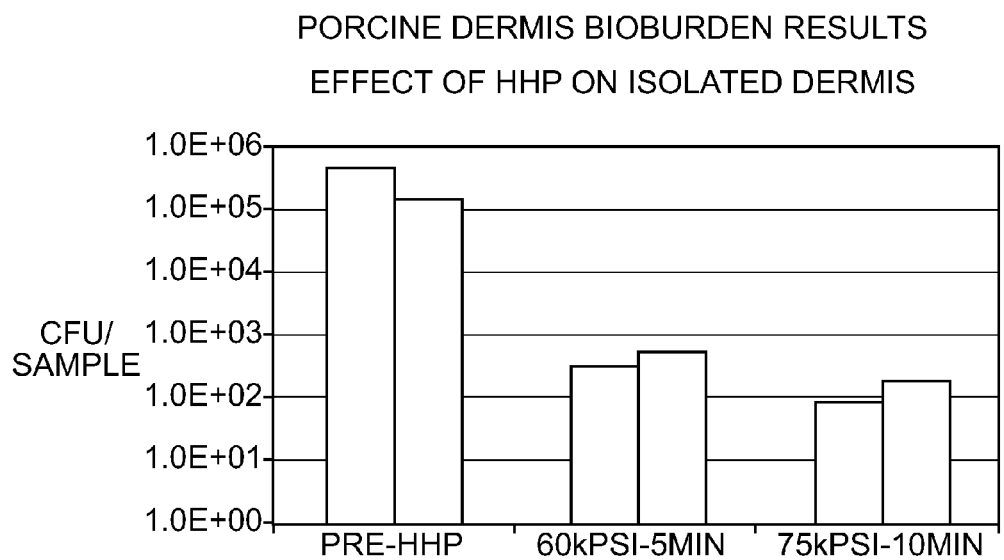
FIG. 2B is bioburden test result data for porcine dermis, as described in Experiment 1.

Bioburden test results are shown in FIGS. 2A and 2B. The data is shown as colony forming units (CFU) per tissue sample, in $LOG_{10}$ scale. The results show at least a 1 to 3 $LOG_{10}$ reduction for non-dehaired tissue and a 4 to 5 $LOG_{10}$ reduction for isolated dermal tissue. The results show that higher pressure and longer pressure hold times reduced the overall bioburden more than a lower pressures and shorter times.

There was a reduction in bacterial deactivation with whole skin tissue, compared to isolated dermal tissue at each pressure tested (60 kPSI and 75 kPSI). Therefore, for dermal grafts, cutting the tissue sample to remove non-dermal components before high hydrostatic pressure treatment can provide improved reduction in bioburden.

In this work, the inactivation data showed excellent results for the short periods tested. However, the DSC properties for processed samples indicated some thermal tissue damage. For example, samples subjected to either 65 kPSI for 5 minutes or 70 kPSI for 10 minutes had thermal onset values on DSC that indicated a high level of denatured collagen. Therefore, experiments were performed to assess the effect of high hydrostatic pressure for decellularization, thawing, or bioburden reduction when the processing temperature was controlled.

EXAMPLE 2

Control of Process Temperature

Porcine skin tissue was obtained and dermal tissue was isolated as described above in Example 1. The tissue was stored at −80° C. prior to use. The samples were then thawed in a convective incubator held at 7° C. for up to 36 hours. All of the samples were cut into approximately 7 cm×7 cm square pieces. Packages were made using the DENI™ Magic Vac packaging to closely fit the dimensions of the tissue.

Tissue samples were placed individually within pre-made packages. PBS was then added to almost fill the package (at least 50 mL on average). The PBS was degassed prior to placement in the packages using a vacuum pull down with agitation for several hours prior to use. Degassing was considered complete when air bubbles were no longer forming around the stir-bar. As much air as possible was removed from the package by squeezing the package, and the open end of the package was sealed with a heat sealer.

Ice was used to cool the high hydrostatic pressure vessel. Approximately 50 lbs of ice was required for a total of three runs. The ice was added to the vessel prior to pressurization, both above and below the tissue. The same pressurization system described in Example 1 was used for the experiments described in Example 2.

Table 2 summarizes the conditions for each run of Example 2. Ice was not used equally because there was a concern that there would be vessel seal leakage at lower temperatures. More ice was used as confidence in the vessel's integrity at low temperature increased. Therefore, the starting temperature of each run was lower as because more ice used.

TABLE 2

Run Conditions for Experiment 2

| Run # | Pressure (PSI) | Time (min) | Start Temp (C.) | Max Temp (C.) |
|---|---|---|---|---|
| 1 | 50,000 | 10 | 11.1 | 23.9 |
| 2 | 50,000 | 30 | 8.6 | 21.3 |
| 3 | 75,000 | 10 | 6.7 | 25.3 |

After high hydrostatic pressure application the tissue was stored under refrigerated conditions (1-10° C.) for no more than 24 hours. To control for effects of the PBS solution on tissue during the time between packaging, treatment, and bioburden testing, untreated control samples were held in PBS and were tested with the treated samples. The samples were cut after high hydrostatic pressure exposure under sterile conditions, which may have affected bioburden results. Bacterial contamination was assessed as in Experiment 1.

Figure 3:
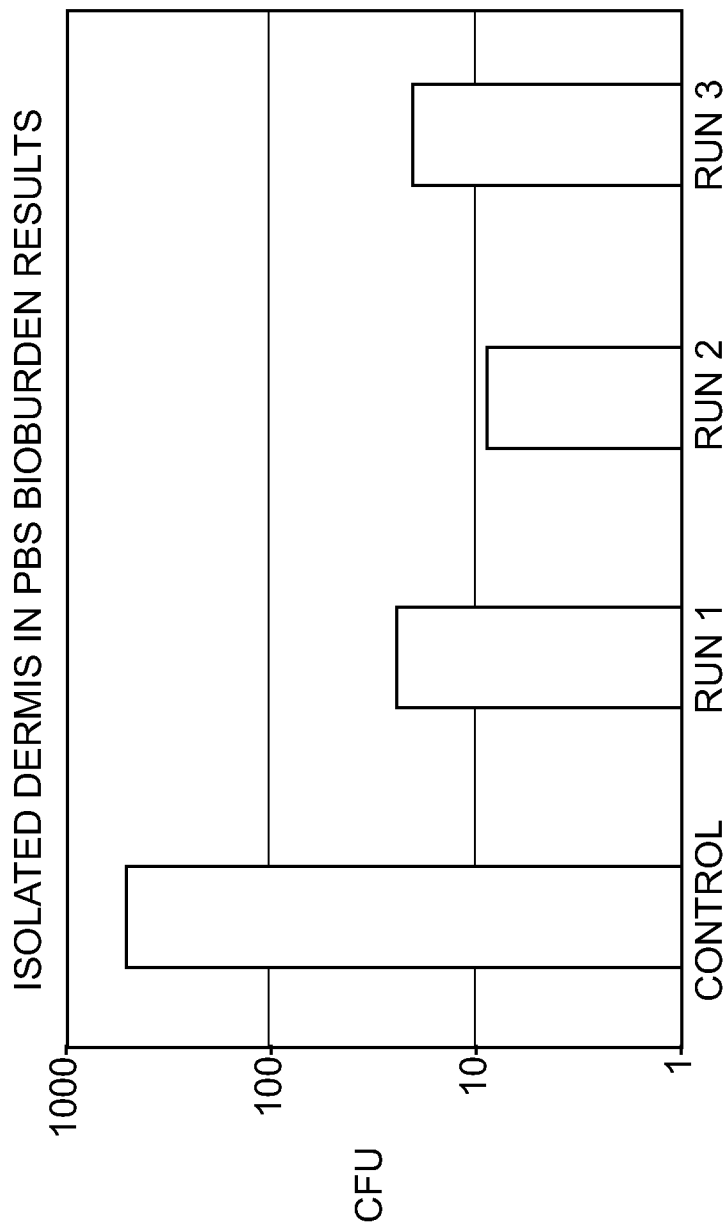
FIG. 3 is bioburden test result data for porcine dermis, as described in Experiment 2.

Bioburden testing was performed as described in Example 1. The bioburden test results are shown in FIG. 3. Only isolated dermal tissue was tested in this study, and the y-axis represents CFUs on a logarithmic scale. The reduction in bioburden improved with longer hold times and higher pressures. For example, Runs 1 and 3 were both performed with 10 minute hold times, but Run 3, which was performed at higher pressure, resulted in increased bioburden reduction. In addition, Runs 1 and 2 were both performed at 50 kPSI, but Run 2, which was performed for a longer time, resulted in increased bioburden reduction compared to Run 1.

Figure 4:
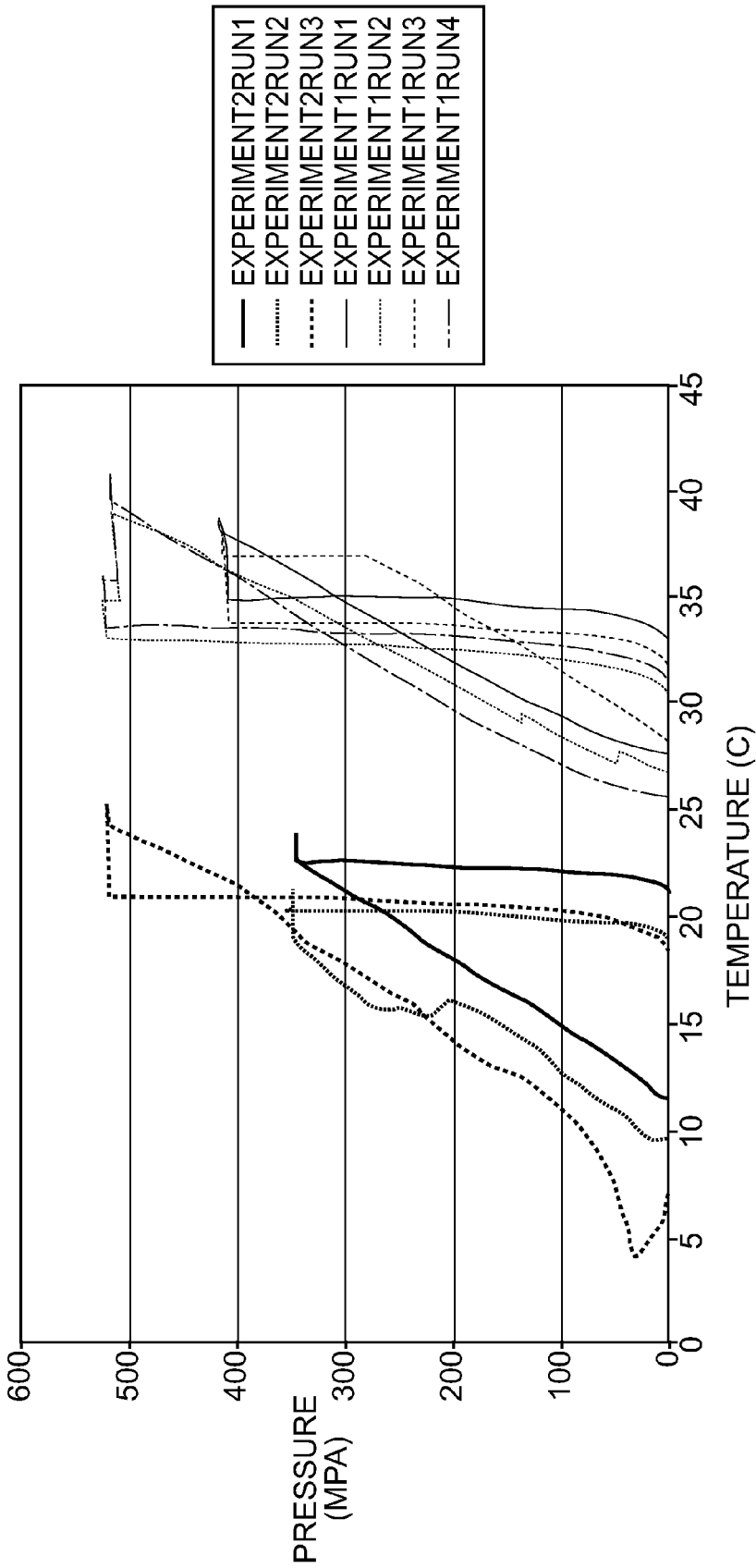
FIG. 4 is the temperature vs. pressure profile curves for the samples of Experiments 1 and 2.

FIG. 4 is a graphical record of the pressure versus temperature during the three runs in this experiment and the four runs of Example 1. In the current experiment, the sample temperatures did not exceed approximately 25° C. In Example 1, the sample temperature exceeded 35° C., and even 40° C. for the higher pressures. The flat region at the top of each curve is a cooling plateau likely due to heat transfer to or from the fluid to the vessel walls during the high pressure hold step. The steel walls of the high pressure vessel started at ambient, and the mass of the steel walls of the vessel provided a massive heat sink or source, depending on the thermal gradient. Example 2 has these cooling plateaus as well, but they are less pronounced.

DSC testing was also performed on each sample using a TA Differential Scanning calorimeter. The DSC results are shown in Table 3. A control, untreated dermal sample is also shown. In contrast to Example 1, the samples in Example 2 did not show low thermal onset values indicative of collagen denaturation. Rather, the thermal onset values for Runs 1 to 3 of Example 2, were approximately 59-60° C., which is similar to the control sample. Therefore, application of high hydrostatic pressure while controlling the sample temperature was effective at reducing the sample bioburden without causing significant collagen denaturation.

TABLE 4

DSC Results for Experiment 2

| Sample | Onset Denaturation Temperature/Enthalphy |
|---|---|
| Control | 60.47/59.17 |
| 1 | 59.84/52.32 |
| 2 | 59.92/59.83 |
| 3 | 60.05/44.43 |

What is claimed is:

1. A method for reducing the bioburden in a soft tissue sample, comprising:
providing a soft tissue sample comprising a mammalian skin containing intact dermal cells and having at least a portion of non-dermal components removed in a container comprising an aqueous solution; and
applying a pressure to the aqueous solution and time sufficient to cause at least a 5 log reduction in a bacterial load of the skin sample and to destroy substantially all of the cells within the skin sample, wherein destroying substantially all of the cells includes disrupting the cell membrane of the cells such that washing the soft tissue sample in a saline solution allows removal of at least 95% of the native skin cells, and wherein applying the pressure includes increasing the pressure at a rate to control a temperature of the skin sample such that the temperature of the skin sample does not exceed 30° C.

2. The method of claim 1, wherein the pressure applied to the aqueous solution is at least 500 MPa.

3. The method of claim 1, wherein the pressure applied to the aqueous solution is at least 300 MPa for at least 30 minutes.

4. The method of claim 1, wherein the pressure applied to the aqueous solution is at least 400 MPa for at least 10 minutes.

5. The method of claim 1, wherein the pressure applied to the aqueous solution is at least 400 MPa for at least 40 minutes.

6. The method of claim 1, wherein the aqueous solution comprises an aqueous salt solution.

7. The method of claim 6, wherein the aqueous solution comprises a phosphate buffered saline.

8. The method of claim 1, further comprising performing a sterilization process on the tissue.

9. The method of claim 8, wherein the sterilization process comprises a gamma irradiation process.

10. The method of claim 8, wherein the sterilization process comprises an e-beam irradiation process.

11. The method of claim 8, wherein the sterilization process comprise a supercritical carbon dioxide sterilization process.

12. The method of claim 8, wherein the sterilization process comprises a peracetic acid treatment process.

13. The method of claim 1, wherein the mammalian tissue comprises porcine dermis.

14. The method of claim 13, further comprising removing an epidermal layer from the skin prior to applying the pressure.

* * * * *